(12) United States Patent
Luo et al.

(10) Patent No.: US 11,362,284 B2
(45) Date of Patent: Jun. 14, 2022

(54) EFFICIENT BLUE-GREEN TO ORANGE-RED THERMALLY ACTIVATED DELAYED FLUORESCENCE MATERIAL, MANUFACTURE METHOD, AND APPLICATION THEREOF

(71) Applicant: WUHAN CHINA STAR OPTOELECTRONICS SEMICONDUCTOR DISPLAY TECHNOLOGY CO., LTD., Wuhan (CN)

(72) Inventors: Jiajia Luo, Wuhan (CN); Xianjie Li, Wuhan (CN); Jinchang Huang, Wuhan (CN); Yu Gu, Wuhan (CN); Lin Yang, Wuhan (CN); Yamei Bai, Wuhan (CN)

(*) Notice: Subject to any disclaimer, the term of this patent is extended or adjusted under 35 U.S.C. 154(b) by 324 days.

(21) Appl. No.: 16/622,955

(22) PCT Filed: Nov. 25, 2019

(86) PCT No.: PCT/CN2019/120751
§ 371 (c)(1),
(2) Date: Dec. 16, 2019

(87) PCT Pub. No.: WO2020/238094
PCT Pub. Date: Dec. 3, 2020

(65) Prior Publication Data
US 2021/0280797 A1  Sep. 9, 2021

(30) Foreign Application Priority Data
May 31, 2019 (CN) .......................... 201910473241.0

(51) Int. Cl.
| H01L 51/00 | (2006.01) |
| C07D 417/04 | (2006.01) |
| C09K 11/06 | (2006.01) |
| H01L 51/50 | (2006.01) |

(52) U.S. Cl.
CPC ........ *H01L 51/0072* (2013.01); *C07D 417/04* (2013.01); *C09K 11/06* (2013.01); *H01L 51/0071* (2013.01); *C09K 2211/1007* (2013.01); *C09K 2211/1018* (2013.01); *H01L 51/5012* (2013.01); *H01L 2251/552* (2013.01)

(58) Field of Classification Search
CPC .. C07D 401/04; C07D 413/04; C07D 417/04; C09K 11/06; C09K 2211/1018; H01L 51/0072
See application file for complete search history.

(56) References Cited

U.S. PATENT DOCUMENTS

| 2018/0233672 A1 | 8/2018 | Ren et al. |
| 2019/0036035 A1 | 1/2019 | Fleming et al. |

FOREIGN PATENT DOCUMENTS

| CN | 105541824 A | 5/2016 |
| CN | 105585577 A | 5/2016 |
| WO | 2017188597 A1 | 11/2017 |

OTHER PUBLICATIONS

Suzuki. Tetrahedron Letters, 2004, 45, 329-333 (Year: 2004).*

\* cited by examiner

*Primary Examiner* — Noble E Jarrell
(74) *Attorney, Agent, or Firm* — JMB Davis Ben-David (57) ABSTRACT

An efficient blue-green to orange-red thermally activated delayed fluorescence material, a manufacture method, and an application thereof are provided. This disclosure solves the technical problems in the art by cleverly synthesizing a series of thermally activated delayed fluorescence materials, which have lower singlet-triplet energy difference, high luminous efficiency, and fast reverse intersystem crossing constant, and simultaneously fine-tuning the structure to cover the spectrum from blue-green light to orange-red light. Further, their structures are confirmed by nuclear magnetic resonance and mass spectroscopy, and their photophysical properties are also determined. Therefore, these luminescent thermally activated delayed fluorescence (TADF) materials are applied to light-emitting layer for manufacturing a series of organic light-emitting diodes (OLEDs) having high performance, which have great application prospects and economic value.

10 Claims, 2 Drawing Sheets

EFFICIENT BLUE-GREEN TO ORANGE-RED THERMALLY ACTIVATED DELAYED FLUORESCENCE MATERIAL, MANUFACTURE METHOD, AND APPLICATION THEREOF

CROSS-REFERENCE TO RELATED APPLICATIONS

This is the U.S. National Stage of International Patent Application No. PCT/CN2019/120751 filed Nov. 25, 2019, which in turn claims the benefit of Chinese Patent Application No. 201910473241.0 filed May 31, 2019.

BACKGROUND OF INVENTION

Field of Invention

The present invention relates to the field of organic electroluminescent diode, and more particularly, to an efficient blue-green to orange-red thermally activated delayed fluorescence material, a manufacturing method, and application thereof.

Description of Prior Art

Organic light-emitting diodes (OLEDs) can actively emit light without backlight, have high luminous efficiency, wide viewing angles, fast response speed, and adaptable to a broad range of temperatures, can be relatively simply manufactured and processed, and also have the advantages of having low driving voltage and low energy consumption, being lighter and thinner, and achieving flexible display, thereby having great application prospects and attracted interest from many researchers. In OLEDs, the luminescent guest materials which play a dominant role are critical. For early OLEDs, used luminescent guest materials were fluorescent materials. Since the exciton ratio of the singlet to the triplet in the OLEDs is 1:3, the theoretical internal quantum efficiency (IQE) of the OLEDs based on fluorescent materials can only reach 25%, which greatly limits the application of the fluorescent electroluminescent devices. The phosphorescent materials with heavy metal complexes can achieve 100% IQE by simultaneously using the singlet and triplet excitons due to their spin-orbit coupling of heavy atoms. However, the heavy metals commonly used are precious metals, such as Ir and Pt, and the phosphorescent materials with heavy metal complexes have yet to be progressed in term of blue light materials. Besides, pure organic thermally activated delayed fluorescence (TADF) materials are cleverly synthesized to have lower singlet-triplet energy difference ($\Delta E_{ST}$), such that the triplet excitons can return to the singlet state by the reverse intersystem crossing (RISC), and then emit light when transiting to the ground state by radiation. Accordingly, it can simultaneously use the singlet and triplet excitons, and also achieve 100% IQE.

For TADF materials, the fast reverse intersystem crossing constant (kRISC) and high photoluminescence quantum yield (PLQY) are required for manufacturing a highly efficient OLED. Currently, in comparison with the heavy metal Jr complexes, the TADF materials having the above properties are still scarce.

Therefore, it is needed to develop a highly efficient blue-green to orange-red thermally activated delayed fluorescence material, which is a compound cleverly synthesized to be a fluorescence material that is capable of achieving the rapid thermal activation of the reverse intersystem crossing constant and the coverage of spectrum from sky blue light to orange-red light, and have great application prospects and economic value.

SUMMARY OF INVENTION

To solve the above technical problems, one of the purposes of the present invention is providing an efficient blue-green to orange-red thermally activated delayed fluorescence material, which achieves ultra-fast reverse intersystem crossing rate and high luminous efficiency.

For such purpose, the efficient blue-green to orange-red thermally activated delayed fluorescence material provided in the present invention includes a compound represented by formula I:

In the compound represented by formula I, $R_1$ is one of the following structures:

-continued and
R₂ is one of the following structures:

Another purpose of the present invention is providing a method of manufacturing the efficient blue-green to orange-red thermally activated delayed fluorescence material, including:
mixing a raw material 1, a raw material 2, palladium acetate, and tri-tert-butylphosphine tetrafluoroborate; and
adding NaOt-Bu, followed by adding toluene under argon for a reaction, thereby obtaining a crude efficient blue-green to orange-red thermally activated delayed fluorescence material (i.e., the above mentioned compound represented by formula I).

In one embodiment, the raw material 1 is 5-bromo-2,3-difluoro-8-phenylquino-6,7-dicarbonitrile.

In one embodiment, the raw material 2 is 9,10-dihydro-9,9-diphenyl acridine, phenoxazine, or phenothiazine.

In one embodiment, a molar ratio of the raw material 1 to the raw material 2 is 1:1 to 1:3, preferably 1:1.2.

In one embodiment, a molar ratio of the palladium acetate, the tri-tert-butylphosphine tetrafluoroborate, and the NaOt-Bu is 1:(3 to 6):(30 to 60), preferably 1:3:30.

In one embodiment, a molar volume ratio of the raw material 1 to toluene is 1:5 to 1:20, preferably 1:8 (mmol: mL).

In one embodiment, a reaction temperature is 8 to 160° C., preferably 120° C.

In one embodiment, a reaction time is 12 to 48 hours, preferably 24 hours.

The method of manufacturing the efficient blue-green to orange-red thermally activated delayed fluorescence material provided in the present invention further includes:
cooling the crude efficient blue-green to orange-red thermally activated delayed fluorescence material;
extracting the crude efficient blue-green to orange-red thermally activated delayed fluorescence material with dichloromethane,
combining organic phases;
mixing with a silica gel under a spinning condition; and
separating and purifying by a column chromatography, thereby obtaining efficient blue-green to orange-red thermally activated delayed fluorescence material.

In one embodiment, the cooling the crude efficient blue-green to orange-red thermally activated delayed fluorescence material is cooling the crude to room temperature, following by pouring it into ice water.

In one embodiment, the frequency of the extracting with dichloromethane is 2 to 4, preferably 3.

The present invention provides a method of manufacturing the efficient blue-green to orange-red thermally activated delayed fluorescence material, including:
mixing a raw material 1, a raw material 2, palladium acetate, and tri-tert-butylphosphine tetrafluoroborate;
adding NaOt-Bu, following by adding toluene under argon, for a reaction, thereby obtaining a crude efficient blue-green to orange-red thermally activated delayed fluorescence material (i.e., the above-mentioned compound represented by formula I);
cooling the crude efficient blue-green to orange-red thermally activated delayed fluorescence material to room temperature, following by pouring into ice water;
extracting the crude efficient blue-green to orange-red thermally activated delayed fluorescence material with dichloromethane;
combining organic phases;
mixing with a silica gel under a spinning condition; and
separating and purifying by a column chromatography, thereby obtaining the efficient blue-green to orange-red thermally activated delayed fluorescence material.

In one embodiment, the raw material 1 is 5-bromo-2,3-difluoro-8-phenylquino-6,7-dicarbonitrile.

In one embodiment, the raw material 2 is 9,10-dihydro-9,9-diphenyl acridine, phenoxazine, or phenothiazine.

In one embodiment, the molar ratio of the raw material 1 to the raw material 2 is 1:1 to 1:3, preferably 1:1.2.

In one embodiment, the molar ratio of the palladium acetate, the tri-tert-butylphosphine tetrafluoroborate, and the NaOt-Bu is 1:(3 to 6):(30 to 60), preferably 1:3:30.

In one embodiment, the molar volume ratio of the raw material 1 to toluene is 1:5 to 1:20, preferably 1:8 (mmol: mL).

In one embodiment, the reaction temperature is 8 to 160° C., preferably 120° C.

In one embodiment, the reaction time is 12 to 48 hours, preferably 24 hours.

In one embodiment, the frequency of the extracting with dichloromethane is 2 to 4, preferably 3.

The present invention provides a method of manufacturing the efficient blue-green to orange-red thermally activated delayed fluorescence material, including:
mixing a raw material 1, a raw material 2, palladium acetate, and tri-tert-butylphosphine tetrafluoroborate;
adding NaOt-Bu, following by adding toluene under argon for a reaction at 120° C. for 24 hours, thereby obtaining a crude efficient blue-green to thermally activated delayed fluorescence material (i.e., the above mentioned compound represented by formula I);

cooling the crude efficient blue-green to orange-red thermally activated delayed fluorescence material to room temperature, following by pouring into ice water;

extracting with dichloromethane;

combining organic phases;

mixing with a silica gel under a spinning condition; and separating and purifying by a column chromatography, thereby obtaining the efficient blue-green to orange-red thermally activated delayed fluorescence material.

In one embodiment, the raw material 1 is 5-bromo-2,3-difluoro-8-phenylquino-6,7-dicarbonitrile.

In one embodiment, the raw material 2 is 9,10-dihydro-9,9-diphenyl acridine, phenoxazine, or phenothiazine.

In one embodiment, the molar ratio of the raw material 1 to the raw material 2 is 1:1.2.

In one embodiment, the molar ratio of palladium acetate, tri-tert-butylphosphine tetrafluoroborate, and NaOt-Bu is 1:3:30.

In one embodiment, the molar volume ratio of the raw material 1 to toluene is 1:8 (mmol:mL).

Another purpose of the present invention is providing a use of the efficient blue-green to orange-red thermally activated delayed fluorescence material.

In one embodiment, the efficient blue-green to orange-red thermally activated delayed fluorescence material is used for manufacturing OLED, especially, for manufacturing the light-emitting layer of OLED.

The present invention has the following advantages:

1) by using different functional groups, the luminescent TADF materials may have superior TADF properties;

2) by using reasonable scheme, the synthesis efficiency of the materials may be improved;

3) the manufacture of organic electroluminescent devices having high efficiency may be achieved; and 4) display devices and electronic devices based on the organic luminescent materials may be manufactured.

TADF materials have a molecular structure in which the electron donor (D) and the electron acceptor (A) are combined, and the present invention achieves the coverage of the emitted light from sky blue light to orange-red light by adjusting the electron donating ability of the donor unit, so as to effectively increase the luminous efficiency of the materials. At the same time, the present invention focuses on the influence of electron donating ability of the electron donor on the material properties. Accordingly, the electroluminescent devices based on the target luminescent TADF materials achieve very high efficiency.

In summary, the present invention solves the technical problems in the art by cleverly synthesising a series of thermally activated delayed fluorescence materials, which have lower singlet-triplet energy difference, high luminous efficiency, and fast reverse intersystem crossing constant, and simultaneously fine-tuning the structure to cover the spectrum from blue-green light to orange-red light. Further, their structures are confirmed by nuclear magnetic resonance and mass spectroscopy, and their photophysical properties are also determined. Therefore, these luminescent TADF materials are applied to light-emitting layer for manufacturing a series of OLEDs having high performance, which have great application prospects and economic value.

BRIEF DESCRIPTION OF DRAWINGS

In order to more clearly illustrate the technical solutions in the embodiments, the drawings described in the description of the embodiments are briefly described below. It is obvious that the drawings in the following description are only some embodiments of the present invention. Other drawings can also be obtained from those skilled persons in the art based on drawings without any creative effort.

DETAILED DESCRIPTION OF PREFERRED EMBODIMENTS

The present invention is described in detail by the following embodiments, but not limited thereto.

The operations not specifically mentioned herein are conventional operations in the art. The materials whose sources are not specifically mentioned herein are commercially available.

As to the sources of raw materials, the raw material 1, (5-bromo-2,3-difluoro-8-phenylquino-6,7-dicarbonitrile), used in the present invention may be commercially available or synthesized referring to the prior art.

The efficient blue-green to orange-red thermally activated delayed fluorescence material provided in the present invention includes a compound represented by formula I:

In the compound represented by formula I, $R_1$ is one of the following structures:

and $R_2$ is one of the following structures:

Based on the matching combinations of $R_1$ and $R_2$, the compound represented by formula I may have 72 specific structures.

Specifically, the compound represented by formula I may be compound 1, compound 2, or compound 3:

Compound 1

Compound 2

Compound 3

The method of manufacturing the efficient blue-green to orange-red thermally activated delayed fluorescence material provided in the present invention includes:

mixing a raw material 1 (5-bromo-2,3-difluoro-8-phenylquino-6,7-dicarbonitrile), a raw material 2 (the raw material 2 is 9,10-dihydro-9,9-diphenyl acridine, phenoxazine, or phenothiazine), palladium acetate, and tri-tert-butylphosphine tetrafluoroborate, in which the molar ratio of the raw material 1 to the raw material 2 is 1:1 to 1:3, preferably 1:1.2;

adding NaOt-Bu (the molar ratio of palladium acetate, tri-tert-butylphosphine tetrafluoroborate, and NaOt-Bu is 1:(3 to 6):(30 to 60), preferably 1:3:30), following by adding toluene under argon (the molar volume ratio of the raw material 1 to toluene is 1:5 to 1:20, preferably 1:8 (mmol: mL)) for a reaction (the reaction temperature is 8 to 160° C., preferably 120° C., and the reaction time is 12 to 48 hours, preferably 24 hours), thereby obtaining a crude efficient blue-green to orange-red thermally activated delayed fluorescence material (i.e., the above-mentioned compound represented by formula I);

cooling the crude efficient blue-green to orange-red thermally activated delayed fluorescence material to room temperature, following by pouring into ice water;

extracting the crude efficient blue-green to orange-red thermally activated delayed fluorescence material with dichloromethane (the frequency is 2 to 4, preferably 3);

combining organic phases;

mixing with a silica gel under a spinning condition; and separating and purifying by a column chromatography, thereby obtaining the efficient blue-green to orange-red thermally activated delayed fluorescence material.

Example 1

Synthesis scheme of target compound 1 is as follows:

Raw material 1

+

Compound 1

Synthesis steps: the raw material 1 (2.09 g, 5 mmol), 9,10-dihydro-9,9-diphenyl acridine (2.00 g, 6 mmol), palladium acetate (45 mg, 0.2 mmol), and tri-tert-butylphosphine tetrafluoroborate (0.17 g, 0.6 mmol) are added into 100 mL two-neck bottle. Further, NaOt-Bu (0.58 g, 6 mmol) is added into the two-neck bottle in a glove box, and then 40 mL toluene deoxygenated and dehydrated beforehand is added under argon for a reaction at 120° C. for 24 hours. Afterward, the reaction mixture is cooled to room temperature and then poured into 200 mL ice water, following by extracting with dichloromethane for 3 times. The organic phases are combined and mixed with a silica gel under a spinning condition, following by separating and purifying by a column chromatography (dichloromethane:n-hexane=3:2 (v:v)). Finally, 1.6 g of sky blue powder (i.e., compound 1) is obtained with a yield of 64%. 1H NMR (300 MHz, CD$_2$Cl$_2$, δ): 7.55-7.46 (s, 5H), 7.19-7.08 (m, 6H), 6.96-6.90 (m, 2H), 1.69 (s, 6H). MS (EI) m/z: [M]+ calcd for C$_{31}$H$_{19}$F$_2$N$_5$, 499.16. found, 499.12.

Example 2

Synthesis scheme of target compound 2 is as follows:

Raw material 1

+

Compound 2

Synthesis steps: the raw material 1 (2.09 g, 5 mmol), phenoxazine (1.10 g, 6 mmol), palladium acetate (45 mg, 0.2 mmol), and tri-tert-butylphosphine tetrafluoroborate (0.17 g, 0.6 mmol) are added into 100 mL two-neck bottle. Further, NaOt-Bu (0.58 g, 6 mmol) is added into the two-neck bottle in a glove box, and then 40 mL toluene deoxygenated and dehydrated beforehand is added under argon for a reaction at 120° C. for 24 hours. Afterward, the reaction mixture is cooled to room temperature and then poured into 200 mL ice water, following by extracting with dichloromethane for 3 times. The organic phases are combined and mixed with a silica gel under a spinning condition, following by separating and purifying by a column chromatography (dichloromethane:n-hexane=3:2 (v:v)). Finally, 1.5 g of green powder is obtained with a yield of 63%. 1H NMR (300 MHz, CD$_2$Cl$_2$, δ): 7.55-7.46 (s, 5H), 7.14-7.07 (m, 2H), 7.01-6.90 (m, 6H). MS (EI) m/z: [M]+ calcd for C$_{28}$H$_{13}$F$_2$N$_5$O, 473.11. found, 473.10.

Example 3

Synthesis scheme of target compound 3 is as follows:

Synthesis steps: the raw material 1 (2.09 g, 5 mmol), phenothiazine (1.19 g, 6 mmol), palladium acetate (45 mg, 0.2 mmol), and tri-tert-butylphosphine tetrafluoroborate (0.17 g, 0.6 mmol) are added into 100 mL two-neck bottle. Further, NaOt-Bu (0.58 g, 6 mmol) is added into the two-neck bottle in a glove box, and then 40 mL toluene deoxygenated and dehydrated beforehand is added under argon for a reaction at 120° C. for 24 hours. Afterward, the reaction mixture is cooled to room temperature and then poured into 200 mL ice water, following by extracting with dichloromethane for 3 times. The organic phases are combined and mixed with a silica gel under a spinning condition, following by separating and purifying by a column chromatography (dichloromethane:n-hexane=3:2 (v:v)). Finally, 1.1 g of orange powder is obtained with a yield of 45%. 1H NMR (300 MHz, $CD_2Cl_2$, δ): 7.55-7.46 (s, 5H), 7.26-7.14 (m, 6H), 7.01-6.96 (m, 2H). MS (EI) m/z: [M]+ calcd for $C_{28}H_{13}F_2N_5S$, 489.09. found, 489.10.

Experimental Example 1

Figure 1:
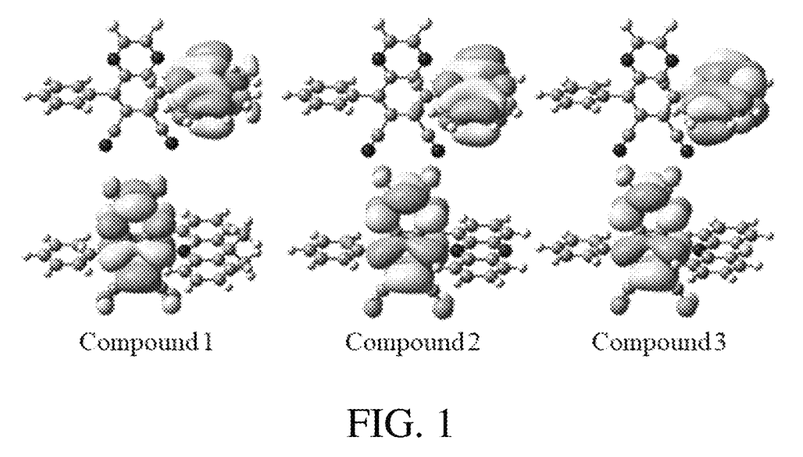
FIG. 1 is a distribution diagram of highest occupied molecular orbital (HOMO) and lowest unoccupied molecular orbital (LUMO) of the target compounds in Experimental example 1, in which the first row is HOMO, and the second row is LUMO.

The distributions of highest occupied molecular orbital (HOMO) and lowest unoccupied molecular orbital (LUMO) of the target compounds obtained by Example 1, Example 2, and Example 3 of the present invention (i.e., Compound 1, Compound 1, and Compound 3) are shown in FIG. 1.

The electrochemical energy levels, i.e., the lowest singlet state (Si) and the lowest triplet (T1) energy level, of the target compounds (i.e., Compound 1, Compound 1, and Compound 3) are reported in the following table:

|  | PL Peak (nm) | $S_1$ (eV) | $T_1$ (eV) | $\Delta E_{ST}$ (eV) | HOMO (eV) | LUMO (eV) |
| --- | --- | --- | --- | --- | --- | --- |
| Compound 1 | 513 | 2.42 | 2.30 | 0.12 | −5.42 | −2.43 |
| Compound 2 | 533 | 2.33 | 2.26 | 0.07 | −5.58 | −2.44 |
| Compound 3 | 570 | 2.18 | 2.10 | 0.08 | −5.60 | −2.43 |

Figure 2:
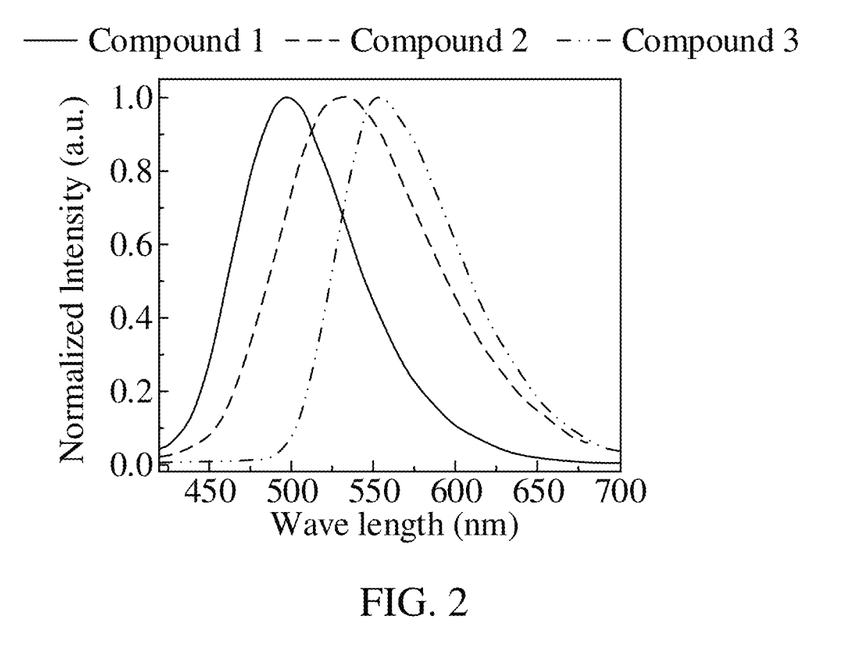
FIG. 2 is the photoluminescence spectroscopy of the target compounds in Experimental example 1.

The photophysical properties of the target compounds (i.e., Compound 1, Compound 1, and Compound 3) are described as follows:

At room temperature, the photoluminescence spectroscopy of the target compounds in toluene solution is shown in FIG. 2, in which the horizontal axis is wavelength and the vertical axis is the normalized intensity. The three curves correspond to compound 1, compound 2 and compound 3 from left to right.

Experimental Example 2

Figure 3:
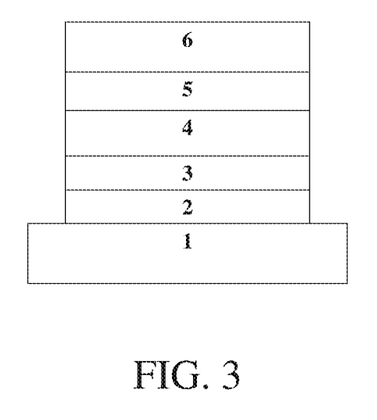
FIG. 3 is a diagram of the electroluminescent device in Experimental example 2.

The electrothermally activated delayed fluorescent device, in which the thermally activated delayed fluorescence material of the present invention is used in the light-emitting layer, may include a substrate layer 1 of glass and conductive glass (ITO), a hole injection layer 2 (MoO3), a transport layer 3 (TCTA), a light-emitting layer 4 (mCBP: the delayed fluorescence material of the present invention), an electron transport layer 5 (1,3,5-tris(3-pyridyl-3-phenyl) benzene (Tm3PyPB)), and a cathode 6 (lithium fluoride/aluminum). The diagram of the electroluminescent device is shown in FIG. 3.

The electroluminescent device may be manufactured according to the conventional process in the art, such as that disclosed in Adv. Mater. 2003, 15, 277. Specifically, the manufacture process is described as follows: MoO3, TCTA, mCBP+thermally activated delayed fluorescence material, TmPyPB, 1 nm LiF, and 100 nm Al are sequentially evaporated on a cleaned conductive glass (ITO) substrate under high vacuum. The device manufactured by this process is shown in FIG. 3, and the structures of the specific devices are as follows:

Device 1 (A1):
ITO/MoO3 (2 nm)/TCTA (35 nm)/mCBP: compound 1 (5% 40 nm)/TmPyPB (40 nm)/LiF (1 nm)/Al (100 nm).

Device 2 (A2):
ITO/MoO3 (2 nm)/TCTA (35 nm)/mCBP: compound 2 (5% 40 nm)/TmPyPB (40 nm)/LiF (1 nm)/Al (100 nm).

Device 3 (A3):
ITO/MoO3 (2 nm)/TCTA (35 nm)/mCBP: compound 3 (5% 40 nm)/TmPyPB (40 nm)/LiF (1 nm)/Al (10 nm).

The current-brightness-voltage property of the device is measured by Keithley source measurement system (Keithley 2400 Sourcemeter, Keithley 2000 Currentmeter) with a calibrated silicon photodiode, and the electroluminescence spectrum is measured by SPEX CCD3000 spectrometer (JY company, France). All measurements are performed at room temperature in the atmosphere. The properties of the devices are reported in the following table:

| Device | Highest current efficiency (cd/A) | CIEx | Maximum external quantum efficiency (%) |
| --- | --- | --- | --- |
| Device 1 | 58.9 | 0.22 | 22.4 |
| Device 2 | 61.3 | 0.24 | 24.6 |
| Device 3 | 43.9 | 0.58 | 19.8 |

The present invention may be applied to the following fields:
1) a blue-green to orange-red TADF material having high efficiency;
2) an electroluminescent device having long lifetime;
3) a display based on the electroluminescent device.

In the above, the present invention has been described in detail by the general descriptions and the preferred embodiments. Based on the present invention, a person skilled in the art may make various modifications and improvements, and such modifications and improvements are obvious for a person skilled in the art. Therefore, the modifications and improvements without departing from the spirit of the present invention fall within the scope of the claims of the present invention.

The subject matter of the present invention may be manufactured and used industrially, thereby having industrial applicability.

What is claimed is:

1. An efficient blue-green to orange-red thermally activated delayed fluorescence material, comprising a compound represented by formula I below:

wherein $R_1$ is one of the following structures:

and
$R_2$ is one of the following structures:

2. A method of manufacturing the efficient blue-green to orange-red thermally activated delayed fluorescence material according to claim 1, comprising:
mixing a raw material 1, a raw material 2, palladium acetate, and tri-tert-butylphosphine tetrafluoroborate; and
adding NaOt-Bu, followed by adding toluene under argon for a reaction, and obtaining a crude efficient blue-green to orange-red thermally activated delayed fluorescence material;
wherein the raw material 1 is 5-bromo-2,3-difluoro-8-phenylquino-6,7-dicarbonitrile, and the raw material 2 is 9,10-dihydro-9,9-diphenyl acridine, phenoxazine, or phenothiazine.

3. The method of manufacturing the efficient blue-green to orange-red thermally activated delayed fluorescence material according to claim 2, wherein a molar ratio of the raw material 1 to the raw material 2 is 1:1 to 1:3.

4. The method of manufacturing the efficient blue-green to orange-red thermally activated delayed fluorescence material according to claim 2, wherein a molar ratio of the palladium acetate, the tri-tert-butylphosphine tetrafluoroborate, and the NaOt-Bu is 1:(3 to 6):(30 to 60).

5. The method of manufacturing the efficient blue-green to orange-red thermally activated delayed fluorescence material according to claim 2, wherein a molar volume ratio of the raw material 1 to toluene is 1:5 to 1:20.

6. The method of manufacturing the efficient blue-green to orange-red thermally activated delayed fluorescence material according to claim 2, wherein a temperature for the reaction is 80 to 160° C., and a time for the reaction is 12 to 48 hours.

7. The method of manufacturing the efficient blue-green to orange-red thermally activated delayed fluorescence material according to claim 2, further comprising:
cooling the crude efficient blue-green to orange-red thermally activated delayed fluorescence material;
extracting the crude efficient blue-green to orange-red thermally activated delayed fluorescence material with dichloromethane;
combining organic phases;
mixing with a silica gel under a spinning condition; and
separating and purifying by column chromatography, thereby obtaining the efficient blue-green to orange-red thermally activated delayed fluorescence material.

8. A method of manufacturing the efficient blue-green to orange-red thermally activated delayed fluorescence material according to claim 1, comprising:
mixing a raw material 1, a raw material 2, palladium acetate, and tri-tert-butylphosphine tetrafluoroborate;
adding NaOt-Bu, following by adding toluene under argon for a reaction, and obtaining a crude efficient blue-green to orange-red thermally activated delayed fluorescence material;
cooling the crude efficient blue-green to orange-red thermally activated delayed fluorescence material to a room temperature, following by pouring into ice water;
extracting the crude efficient blue-green to orange-red thermally activated delayed fluorescence material with dichloromethane;
combining organic phases;
mixing with a silica gel under a spinning condition; and
separating and purifying by column chromatography, and obtaining the efficient blue-green to orange-red thermally activated delayed fluorescence material;
wherein the raw material 1 is 5-bromo-2,3-difluoro-8-phenylquino-6,7-dicarbonitrile, and the raw material 2 is 9,10-dihydro-9,9-diphenyl acridine, phenoxazine, or phenothiazine;
wherein a molar ratio of the raw material 1 to the raw material 2 is 1:1 to 1:3, a molar ratio of the palladium acetate, the tri-tert-butylphosphine tetrafluoroborate, and the NaOt-Bu is 1:(3 to 6):(30 to 60); a molar volume ratio of the raw material 1 to toluene is 1:5 to 1:20; and
wherein a reaction temperature is 80 to 160° C., a reaction time is 12 to 48 hours, and a frequency of the extracting with dichloromethane is 2 to 4.

9. An organic light-emitting diode (OLED) device comprising the efficient blue-green to orange-red thermally activated delayed fluorescence material of claim 1.

10. The OLED device according to claim 9, wherein the efficient blue-green to orange-red thermally activated delayed fluorescence material is used for manufacturing a light-emitting layer of the OLED device.

* * * * *